United States Patent
Hiei et al.

(10) Patent No.: US 10,274,218 B2
(45) Date of Patent: Apr. 30, 2019

(54) AIR-CONDITIONING CONTROL SYSTEM

(71) Applicant: DAIKIN INDUSTRIES, LTD., Osaka-shi, Osaka (JP)

(72) Inventors: Takehiko Hiei, Osaka (JP); Kazuhisa Shigemori, Osaka (JP); Noriyuki Okuda, Osaka (JP)

(73) Assignee: DAIKIN INDUSTRIES, LTD., Osaka-Shi (JP)

( * ) Notice: Subject to any disclaimer, the term of this patent is extended or adjusted under 35 U.S.C. 154(b) by 0 days.

(21) Appl. No.: 15/746,518

(22) PCT Filed: Jun. 3, 2016

(86) PCT No.: PCT/JP2016/002693
§ 371 (c)(1),
(2) Date: Jan. 22, 2018

(87) PCT Pub. No.: WO2017/022156
PCT Pub. Date: Feb. 9, 2017

(65) Prior Publication Data
US 2018/0231269 A1    Aug. 16, 2018

(30) Foreign Application Priority Data
Jul. 31, 2015    (JP) .................................. 2015-152254

(51) Int. Cl.
*F24F 11/30* (2018.01)
*F24F 11/65* (2018.01)
(Continued)

(52) U.S. Cl.
CPC ................ *F24F 11/65* (2018.01); *A61B 5/02* (2013.01); *A61B 5/0205* (2013.01); *A61B 5/11* (2013.01);
(Continued)

(58) Field of Classification Search
CPC . F24F 11/65; F24F 11/56; F24F 11/30; G05B 15/02; A61B 5/11; A61B 5/0205
See application file for complete search history.

(56) References Cited

U.S. PATENT DOCUMENTS

| | | | |
|---|---|---|---|
| 2009/0124926 A1* | 5/2009 | Funakura | F24F 11/30 600/555 |
| 2009/0276062 A1* | 11/2009 | Kanai | G16H 50/20 700/45 |

(Continued)

FOREIGN PATENT DOCUMENTS

| | | |
|---|---|---|
| JP | 9-14719 A | 1/1997 |
| JP | 2003-42509 A | 2/2003 |

(Continued)

OTHER PUBLICATIONS

International Search Report, issued in PCT/JP2016/002693, dated Aug. 23, 2016.

*Primary Examiner* — Vincent H Tran
(74) *Attorney, Agent, or Firm* — Birch, Stewart, Kolasch & Birch, LLP

(57) ABSTRACT

This system correctly obtains a thermal sensation of a person in a room to provide a comfortable environment. A first parameter deriver derives, as a first parameter, a ratio of a low frequency component to a high frequency component in a variation of R-R intervals of a person, based on his/her body movement. A second parameter deriver derives, as a second parameter, any one of a coefficient of variation of R-R intervals, a respiration rate, or a heart rate of the person, based on the body movement of the person. An estimator estimates a thermal sensation of the person, based on the first parameter and the second parameter. A CPU for air-conditioning control controls an air-conditioning capacity of the air conditioner, based on a result of the estimation by the estimator.

7 Claims, 8 Drawing Sheets

(51) Int. Cl.

| | | |
|---|---|---|
| *A61B 5/02* | (2006.01) | |
| *A61B 5/11* | (2006.01) | |
| *G16H 10/60* | (2018.01) | |
| *A61B 5/0205* | (2006.01) | |
| *A61B 5/00* | (2006.01) | |
| *G05B 15/02* | (2006.01) | |
| *F24F 11/62* | (2018.01) | |
| *F24F 120/12* | (2018.01) | |
| *F24F 120/14* | (2018.01) | |
| *F24F 11/56* | (2018.01) | |
| *H04R 1/08* | (2006.01) | |

(52) U.S. Cl.
CPC ............ *A61B 5/4035* (2013.01); *F24F 11/62* (2018.01); *G05B 15/02* (2013.01); *G16H 10/60* (2018.01); *F24F 11/56* (2018.01); *F24F 2120/12* (2018.01); *F24F 2120/14* (2018.01); *F24F 2221/38* (2013.01); *H04R 1/08* (2013.01)

(56) References Cited

U.S. PATENT DOCUMENTS

| | | | |
|---|---|---|---|
| 2010/0234747 | A1 | 9/2010 | Hatakeyama |
| 2013/0048263 | A1* | 2/2013 | Nouvel .................... F24F 11/30 |
| | | | 165/237 |
| 2015/0045981 | A1* | 2/2015 | Mise ...................... G05D 23/19 |
| | | | 700/300 |
| 2015/0204556 | A1* | 7/2015 | Kusukame ......... B60H 1/00742 |
| | | | 165/237 |
| 2016/0374606 | A1* | 12/2016 | Shikii ...................... A61B 5/18 |
| | | | 600/301 |
| 2017/0242412 | A1* | 8/2017 | Kim ....................... G05B 15/02 |

FOREIGN PATENT DOCUMENTS

| | | |
|---|---|---|
| JP | 2009-39167 A | 2/2009 |
| JP | 2009-228931 A | 10/2009 |
| JP | 2010-236732 A | 10/2010 |
| JP | 2011-83498 A | 4/2011 |

* cited by examiner

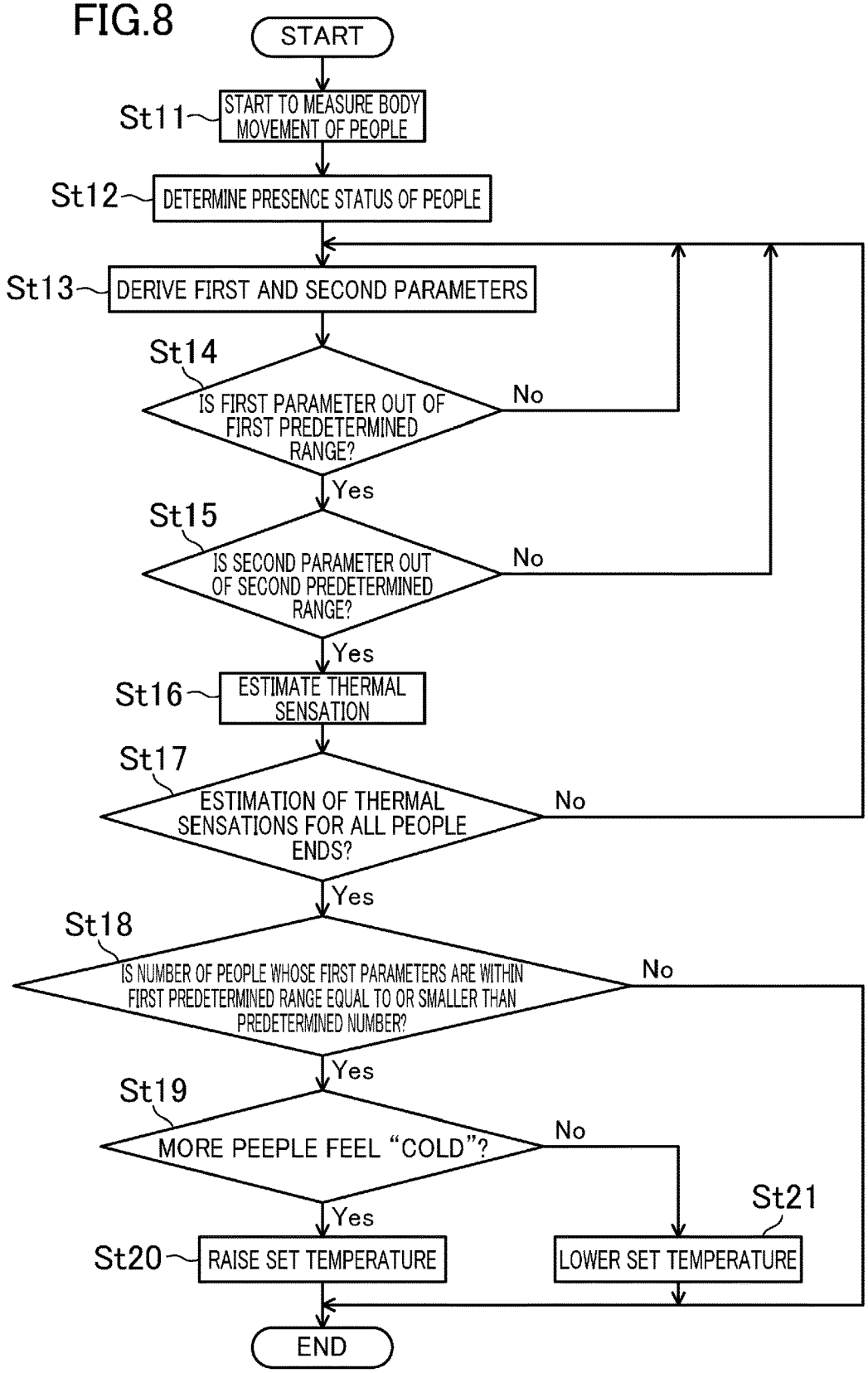

AIR-CONDITIONING CONTROL SYSTEM

TECHNICAL FIELD

The present invention relates to a system to control an air conditioner.

BACKGROUND ART

Patent Document 1 describes a method for controlling an air conditioner in a space to be air-conditioned. Patent Document 1 discloses a technique to measure which of the sympathetic nerve and the parasympathetic nerve of a person in a room is more active, and, based on the measurement result, to warm or cool the person.

CITATION LIST

Patent Document

Patent Document 1: Japanese Unexamined Patent Publication No. 2011-83498

SUMMARY OF THE INVENTION

Technical Problem

Even though the person in the room feels uncomfortable because his or her sympathetic nerve is more active than parasympathetic nerve, the determination in which of the nerves is more active alone has difficulty in understanding that the person feels uncomfortable because the person feels whether "hot" or "cold" (hereinafter referred to as "thermal sensation" of a person in a room).

Whereas, Patent Document 1 discloses a technique to provide a sensor to measure a body temperature or a perspiration level of a person in a room separately from a sensor to measure which of the sympathetic nerve or the parasympathetic nerve is more active. This technique makes it possible to understand the thermal sensation of the person in the room based on the body temperature or the perspiration level of the person when his or her sympathetic nerve is more active.

However, the above technique of Patent Document 1 requires at least two sensors to be always attached to the body of the person in the room. Hence, the person feels uncomfortable with the presence of two sensors attached to his or her body. As a result, the sympathetic nerve could basically become more active. Accordingly, it could be difficult to correctly obtain a thermal sensation of the person.

The present invention is conceived in view of the above problems, and intends to correctly obtain a thermal sensation of a person in a room and provide a comfortable environment, using a single sensor.

Solution to the Problem

A first aspect of the present disclosure is directed to an air-conditioning control system. The air-conditioning control system includes: a measurer (21,23) measuring a body movement of a person (E) in a room a space (S) of which is to be air-conditioned by an air conditioner (A); a first parameter deriver (28a) deriving, as a first parameter, a ratio of a low frequency component to a high frequency component (LF/HF) in a variation of R-R intervals of the person (E), based on a result of the measurement by the measurer (21,23); a second parameter deriver (28b) deriving, as a second parameter, any one of a coefficient of variation of R-R intervals (CVRR), a respiration rate (RR), or a heart rate (HR) of the person (E), based on the result of the measurement by the measurer (21,23); an estimator (28c) estimating a thermal sensation of the person (E), based on the first parameter and the second parameter; and an air-conditioning controller (48) controlling an air-conditioning capacity of the air conditioner (A), based on a result of the estimation by the estimator (28c).

Here, the body movement of the person (E) is measured only by the measurer (21, 23). From one of the results of the measurement, derived are (i) the first parameter (specifically, the ratio of the low frequency component to the high frequency component (LF/HF) in the variation of R-R intervals of the person (E)) and (ii) the second parameter (specifically, one of the coefficient of variation of R-R intervals (CVRR), the respiration rate (RR), or the heart rate (HR)) of the person (E). Then, the thermal sensation of the person (E) is estimated from the first parameter and the second parameter. Based on the estimated thermal sensation, the air conditioner (A) is controlled. Specifically, even though one measurer—the minimum number of measures—is provided as a sensor, the air-conditioning control system (10) can obtain multiple parameters for the person (E). Furthermore, the combination of the first and second parameters is a combination of (i) the ratio of the low frequency component to the high frequency component (LF/HF) which makes it possible to understand whether the person (E) feels uncomfortable and (ii) one of the indexes which relate to a condition of the body and the thermal sensation of the person (E); namely one of the coefficient of variation of R-R intervals (CVRR), the respiration rate (RR), or the heart rate (HR). Hence, using the combination of the parameters, the air-conditioning control system (10) can correctly obtain the thermal sensation of the person (E) to provide the space (S) with comfortable environment.

In a second aspect directed to the air-conditioning control system of the first aspect, the measurer (21, 23) may measure the body movement of the person (E) without restraining the person (E).

Here, the body movement of the person (E) can be measured without restraining the person (E). Specifically, the measurer (21, 23) as a sensor is not always attached to the body of the person (E). Hence, the person (E) is free from an uncomfortable feeling caused when a sensor is always attached to the person (E).

In a third aspect directed to the air-conditioning control system of claim 1 or claim 2, the first parameter may be characterized to be represented in a quadratic function opening up where a temperature in the space (S) is a variable, the second parameter may be characterized to vary linearly where the temperature in the space (S) is the variable, and if the first parameter is out of a first predetermined range, the estimator (28c) may carry out operation to determine whether the thermal sensation of the person (E) is hot or cold based on the second parameter.

The ratio of the low frequency component to the high frequency component (LF/HF) (i.e., the first parameter) is also interpreted as an index to indicate whether the person (E) feels comfortable or uncomfortable. If the ratio of the low frequency component to the high frequency component (LF/HF) is out of the first predetermined range, the estimator (28c) can determine that the person (E) feels uncomfortable. Hence, from a value of the second parameter linearly changing depending on a temperature (i.e., one of the coefficient of variation of R-R intervals (CVRR), the respiration rate (RR), or the heart rate (HR)), the estimator (28c)

can determine the reason why the person (E) feels uncomfortable is whether the person (E) is "hot" or "cold". Using the first parameter characterized to be represented in a quadratic function where the temperature is a variable and the second parameter characterized to be represented in a straight line where the temperature is the variable, the air-conditioning control system (10) can correctly determine the thermal sensation of the person (E).

In a fourth aspect directed to the air-conditioning control system of the third aspect, the estimator (28c) may carry out the operation if the second parameter is out of a second predetermined range.

For example, if the first parameter is out of the first predetermined range, the second parameter is also determined to be presumably out of the second predetermined range. In this case, if the first parameter is out of the first predetermined range and the second parameter is also out of the second predetermined range, the result of the measurement by the measurer (21, 23) and the derived first and second parameters can be determined as normal values. Use of the normal first and second parameters makes it possible to estimate the thermal sensation of the person (E) and control the operation of air conditioner (A) with accuracy.

In a fifth aspect directed to the air-conditioning control system of the fourth aspect, the estimator (28c) may suspend the operation if the second parameter is within the second predetermined range.

In the case where the second parameter is within the second predetermined range even though the first parameter is out of the first predetermined range, some kind of problem is assumed to happen to either the derived first parameter or second parameter. If the above determination operation is carried out using such a problematic parameter, the estimator (28c) could falsely determine whether the person (E) feels hot or cold. Based on the result of the false determination, the air-conditioning control system (10) would cause the air conditioner (A) to carry out undesirable operation for the person (E). Whereas, in this aspect, the determination operation is suspended if the second parameter is within the second predetermined range even though the first parameter is out of the first predetermined range. Such a feature can avoid the use of a problematic parameter followed by false determination of the thermal sensation of the person (E), and operation of the air conditioner (A) based on the result of the false determination.

In a sixth aspect directed to the air-conditioning control system of any one of the third to fifth aspects, the air-conditioning controller (48) may determine, as a set temperature for the air conditioner (A), a temperature observed when the first parameter represented in the quadratic function has a minimum value.

As already described, the ratio of the low frequency component to the high frequency component (LF/HF); namely the first parameter, is characterized to be represented in a quadratic function opening up where the temperature is a variable. The temperature observed when the first parameter has the minimum value xa is to be a temperature for the person (E) to feel comfortable. Since this air-conditioning control system (10) determines the set temperature of the air conditioner (A) to be a temperature observed when the first parameter has the minimum value xa. Hence, the temperature in the space (S) eventually comes to a level in which the person (E) feels comfortable.

In a seventh aspect directed to the air-conditioning control system of any one of the first to sixth aspects, if the person (E) includes people (E1, E2, E3), and the people (E1, E2, E3) are in the space (S), for each of the people (E1, E2, E3), the first parameter deriver (28a) may derive the first parameter and the second parameter deriver (28b) may derive the second parameter, the estimator (28c) may estimate a thermal sensation for each of the people (E1, E2, E3), using the first parameter and the second parameter for each of the people (E1, E2, E3), and if more than a predetermined number of the people (E1, E2, E3) have the thermal sensation of either hot or cold, the air-conditioning controller (48b) may control the air-conditioning capacity of the air conditioner (A) in accordance with the thermal sensation of either hot or cold shared with a majority of the people (E1, E2, E3) having the thermal sensation of either hot or cold.

In this aspect, if multiple people (E1, E2, E3) are in the space (S), the operation of the air conditioner (A) is controlled in accordance with a thermal sensation of either "hot" or "cold" shared with a majority of the people (E1, E2, E3) having the thermal sensation of either "hot" or "cold." Such a feature provides the space (S) with a comfortable environment for the majority of the people (E1, E2, E3).

In an eight aspect directed to the air-conditioning control system of the seventh aspect, the measurer (21, 23) may include measurers (21, 23), and each of the measurers (21, 23) may be provided to a corresponding one of chairs (G1, G2, G3) in the space (S), and may measure a body movement of the people (E1, E2, E3) sitting on the chairs (G1, G2, G3), the air-conditioning control system further comprising a presence status determiner (48a) determining a presence status of the people (E1, E2, E3) sitting on the chairs (G1, G2, G3), based on a result of the measurements by the measurers (21, 23).

Thanks to this feature, the body movements of the people (E1, E2, E3) are easily measured while the people (E1, E2, E3) are simply sitting on the chairs (G1, G2, G3). The thermal sensations of the people (E1, E2, E3) sitting on the chairs (G1, G2, G3) are the factors to be included for the control of the air-conditioning capacity. Such a feature eliminates the need for previously storing, in a memory, position information on the chairs (G1, G2, G3) and the people (E1, E2, E3). Moreover, even if the people (E1, E2, E3) temporarily sit on different chairs (G1, G2, G3), the air-conditioning control system (10) can obtain thermal sensations of the people (E1, E2, E3) sitting on the different chairs (G1, G2, G3) at that moment.

Advantages of the Invention

The first aspect of the present disclosure allows the air-conditioning control system (10) to correctly obtain the thermal sensation of the person (E) to provide the space (S) with comfortable environment, using a minimal number of measurers (21, 23) as a sensor.

The second aspect allows the person (E) to be free from an uncomfortable feeling caused when a sensor is always attached to the person (E).

The third aspect allows the air-conditioning control system (10) to correctly obtain a thermal sensation of the person (E).

The fourth aspect makes it possible, with accuracy, to estimate the thermal sensation of the person (E) and control operation of the air conditioner (A).

The fifth aspect makes it possible to avoid a false determination of the thermal sensation of the person (E), and operation of the air conditioner (A) based on the result of the false determination.

The sixth aspect makes the temperature in the space (S) to eventually come to a level in which the person (E) feels comfortable.

The seventh aspect allows the space (S) to be provided with a comfortable environment for a majority of the people (E1, E2, E3).

The eighth aspect eliminates the need for previously storing, in a memory, information on the person (E) sitting on the chair (G). Moreover, even if the people (E1, E2, E3) temporarily sit on different chairs (G1, G2, G3), the eighth aspect makes it possible to obtain the thermal sensations of the people (E1, E2, E3) sitting on the different chairs (G1, G2, G3) at that moment.

BRIEF DESCRIPTION OF THE DRAWINGS

FIG. 8 is a flowchart indicating a sequence of operation performed by the air-conditioning control system according to the second embodiment.

DETAILED DESCRIPTION

Embodiments of the present invention will now be described in detail with reference to the drawings. The following embodiments are merely exemplary ones in nature, and are not intended to limit the scope, applications, or use of the present invention.

First Embodiment

<Outline>

An air-conditioning control system (10) according to this embodiment estimates a thermal sensation of a person (E) in a room whose space (S) is to be air-conditioned by an air conditioner (A), and controls operation of the air conditioner (A) depending on the estimated thermal sensation.

In particular, the air-conditioning control system (10) measures a body movement of the person (E) while the person (E) simply sits on a chair (G) set in the space (S) without restraining the person (E). From a result of the measurement, the air-conditioning control system (10) then derives multiple parameters for heartbeat and breathing of the person (E). The air-conditioning control system (10) can correctly estimate the thermal sensation of the person (E), using the derived multiple parameters.

Here, an arrangement of such items as appliances and furniture in the space (S) is described with reference to FIG. 1. In this embodiment, the space (S) is for example a private room in such a building as an office and an ordinary house.

One air conditioner (A) is installed for the space (S). The air conditioner (A) is placed on a floor in a space located across a sidewall (S1) from the space (S). The air conditioner (A) is connected through a duct to an air outlet (S1a) formed on the sidewall (S1) of the space (S) and close to a ceiling (S2). The air conditioner (A) supplies conditioned air into the space (S) through the air outlet (S1a).

Moreover, in the space (S), a desk (F) for the person (E) to work at and a chair (G) for the desk (F) are provided. A personal computer (P) is placed on the desk (F).

<Configuration of Air-Conditioning Control System>

Figure 1:
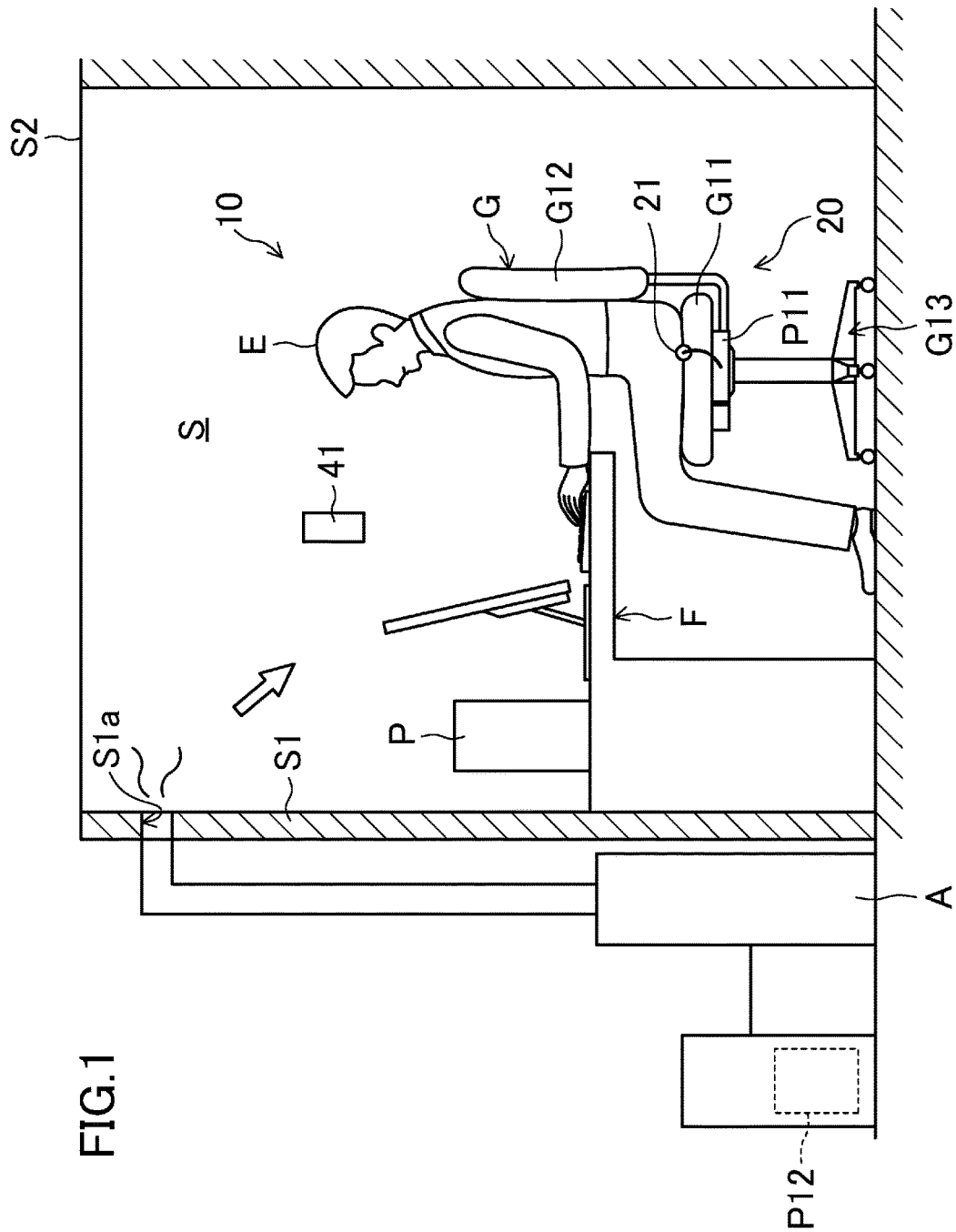
FIG. 1 is a schematic view illustrating a configuration of an air-conditioning control system according to a first embodiment.
Figure 2:
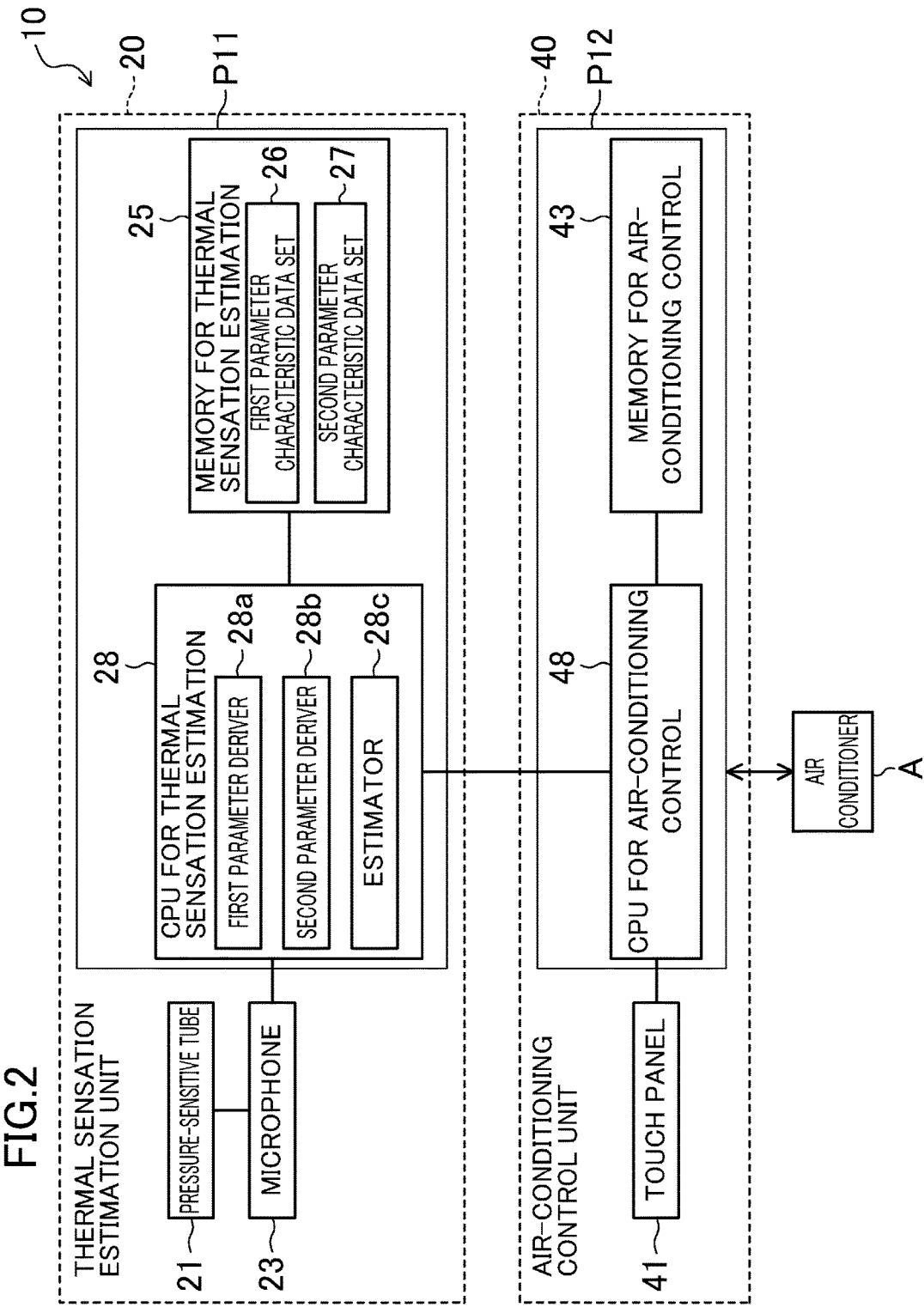
FIG. 2 is a block diagram schematically illustrating a configuration of the air-conditioning control system according to the first embodiment.

As illustrated in FIGS. 1 and 2, the air-conditioning control system (10) includes: a thermal sensation estimation unit (20); and an air-conditioning control unit (40). The thermal sensation estimation unit (20) is secured to the chair (G) on which the person (E) sits. The air-conditioning control unit (40) is provided across the interior and the vicinity of the space (S). The thermal sensation estimation unit (20) and the air-conditioning control unit (40) are communicably connected to each other.

—Thermal Sensation Estimation Unit—

Figure 3:
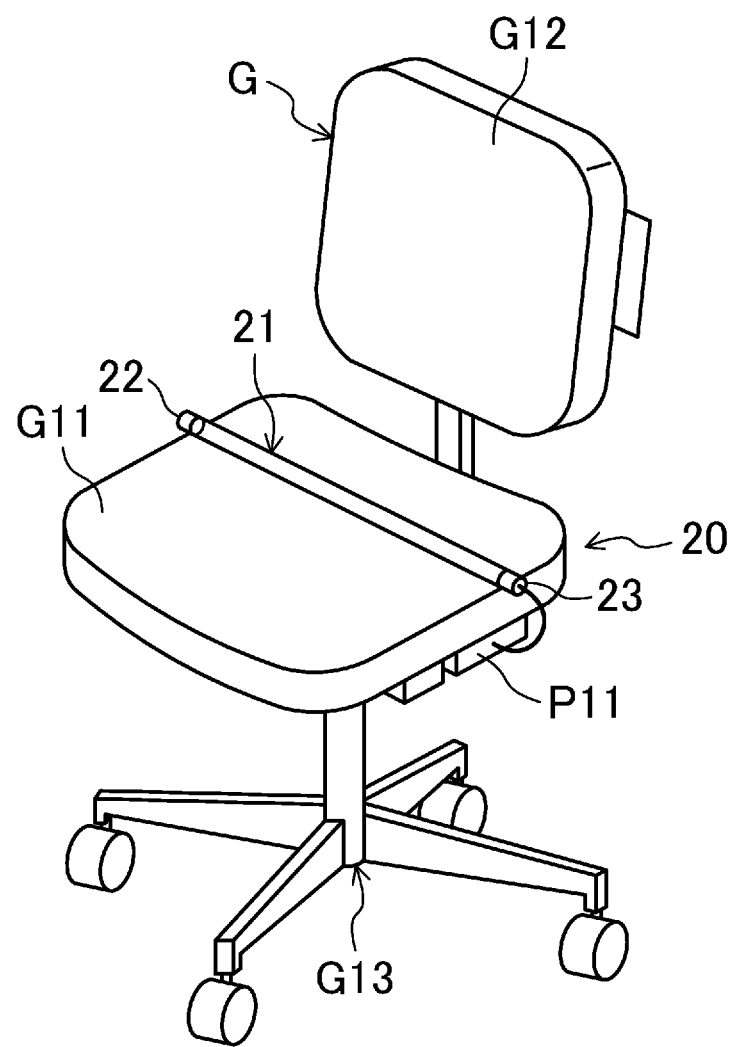
FIG. 3 is an external view of a chair with a thermal sensation estimator secured to the chair.

The thermal sensation estimation unit (20) derives multiple parameters for, for example, a current heartbeat of the person (E) to estimate a thermal sensation (any one of "hot", "cold", or "neither of them (neutral)") of the person (E). As illustrated mainly in FIG. 2, the thermal sensation estimation unit (20) includes: a pressure-sensitive tube (21); a microphone (23); a memory for thermal sensation estimation (25); and a central processing unit (CPU) for thermal sensation estimation (28). As illustrated in FIGS. 1 and 3, the pressure-sensitive tube (21) and the microphone (23) are provided to a seat (G11) of the chair (G). As illustrated in FIG. 2, the memory for thermal sensation estimation (25) and the CPU for thermal sensation estimation (28) are mounted on a single printed board (P11). As illustrated in FIGS. 1 and 3, the printed board (P11) is provided to a rear face of the seat (G11); that is, toward a leg (G13) supporting the seat (G11). Moreover, the seat (G11) is provided with a battery (not shown) to be used as a power supply of the thermal sensation estimation unit (20).

Note that the printed board (P11) and the battery may be secured not to the seat (G11) but to a back (G12).

The pressure-sensitive tube (21) and the microphone (23) described below correspond to a "measurer" measuring the body movement of the person (E) in the space (S).

—Pressure-Sensitive Tube—

The pressure-sensitive tube (21) is made of such a resin material as polyvinyl chloride (PVC) and silicone, and shaped into a cylinder. In this embodiment, as an example, the pressure-sensitive tube (21) is provided toward the rear of the seat (G11) with respect to the center in a front-to-back direction, and linearly extends in a right-to-left direction (the right-to-left direction in FIG. 3). Specifically, the pressure-sensitive tube (21) is provided for the hip and the thighs of the person (E) sitting on the chair (G).

A seal (22) is inserted into an opening at an end (the left end in FIG. 3) of the pressure-sensitive tube (21). The seal (22) blocks the end of the pressure-sensitive tube (21). The microphone (23) is inserted into an opening on another end (the right end in FIG. 3) of the pressure-sensitive tube (21). The microphone (23) blocks the other end of the pressure-sensitive tube (21).

Specifically, the pressure-sensitive tube (21) is hollow and tightly sealed.

—Microphone—

The microphone (23) is connected to an end of the pressure-sensitive tube (21). The microphone (23) acts as a pressure receiver (a pressure sensor) receiving an internal pressure of the pressure-sensitive tube (21).

Specifically, when the person (E) sits on the seat (G11), the internal pressure of the pressure-sensitive tube (21) changes with the change in body movement of the person (E). This change in internal pressure is received by the microphone (23). The microphone (23) lets a signal (a pressure signal) generated in accordance with a level of the pressure pass through a not-shown filter, and then outputs the signal to the CPU for thermal sensation estimation (28).

As described above, the "measurer" according to this embodiment is not a sensor either having constant physical contact with the person (E) or restraining at least a part (an arm, for example) of the body of the person (E), unlike a sensor to measure a blood flow rate, for example. The "measurer" according to this embodiment is a sensor to measure the body movement of the person (E) while the person (E) simply sits on the chair (G) without restraining the person (E).

—Memory for Thermal Sensation Estimation—

The memory for thermal sensation estimation (25) includes such a semiconductor memory as a flash memory, and such a recording medium as a hard disc. The memory for thermal sensation estimation (25) stores a first parameter characteristic data set (26) and a second parameter characteristic data set (27), in addition to various programs to be read by the CPU for thermal sensation estimation (28) so that the CPU for thermal sensation estimation (28) executes various functions described below.

The first parameter characteristic data set (26) and the second parameter characteristic data set (27) are used when the CPU for thermal sensation estimation (28) determines the thermal sensation of the person (E) in accordance with the pressure signal output by the microphone (23). Either data set (26, 27) is previously stored in the memory for thermal sensation estimation (25) before the air-conditioning control system (10) is installed. Each of the parameter characteristic data sets (26, 27) is described below.

—First Parameter Characteristic Data Set—

The first parameter characteristic data set (26) indicates characteristics of a first parameter. The first parameter is a ratio of a low frequency component to a high frequency component (LF/HF) in variation of R-R intervals of the person (E).

The ratio (LF/HF) of the low frequency component to the high frequency component; namely the first parameter, indicates as an index a balance between the sympathetic nerve and the parasympathetic nerve (i.e., an autonomic balance) of the person (E). Either "HF" or "LF" corresponds to one of two peaks obtained when a frequency analysis is performed on the variation of R-R intervals. The component "HF" denotes a high frequency component (e.g., 0.20 Hz or higher), and the component "LF" denotes a low frequency component (e.g., ranging from 0.05 Hz to 0.20 Hz). The component "HF" appears when the parasympathetic nerve is more active than the sympathetic nerve (i.e., when the parasympathetic nerve is activated). The component "LF" appears when either one of the sympathetic nerve or the parasympathetic nerve is more active than the other (i.e., when either one of the sympathetic nerve or the parasympathetic nerve is activated). Hence, the more the person (E) is in an excessively stressed state in which the sympathetic nerve is active, the higher the ratio (LF/HF) of the low frequency component to the high frequency component (i.e., the first parameter) is. This shows that the person (E) is out of the autonomic balance. In contrast, the parasympathetic nerve is more active when the person (E) is in a relaxed state than in an excessively stressed state. Thus, the ratio (LF/HF) of the low frequency component to the high frequency component (i.e., the first parameter) becomes low. This shows that the person (E) is in the autonomic balance.

Thus, the ratio (LF/HF) of the low frequency component to the high frequency component (i.e., the first parameter) is also interpreted as an index to indicate whether the person (E) feels the space (S) comfortable. As the first parameter indicates a higher value, the person (E) feels more uncomfortable, and as the first parameter indicates a lower value, the person (E) feels comfortable more sufficiently.

Figure 4:
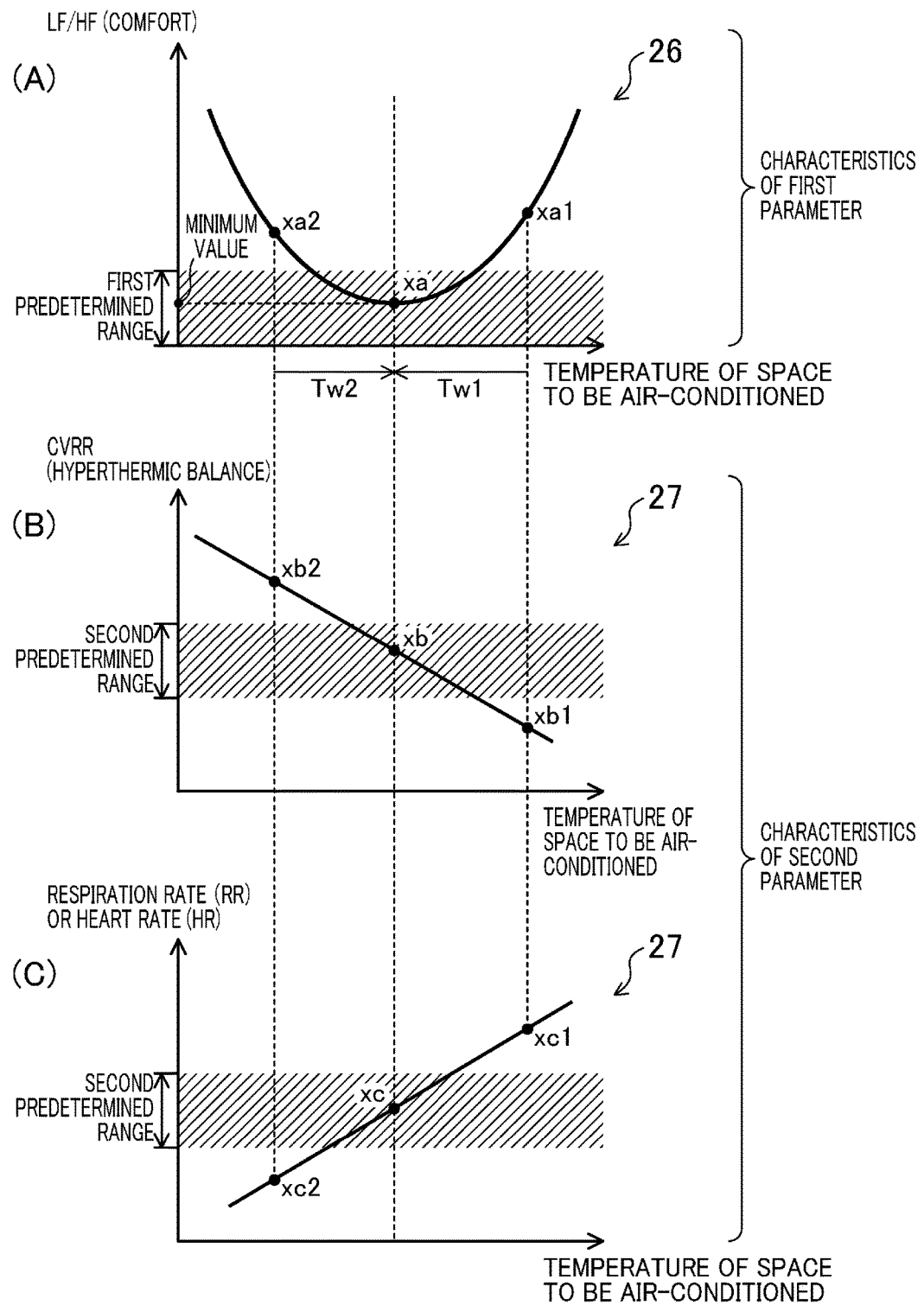
FIG. 4 is a set of graphs illustrating concepts of a first parameter characteristic data set and a second parameter characteristic data set.

As illustrated in a graph (A) of FIG. 4, this first parameter is characterized to be represented in a quadratic function, using a temperature in the space (S) (i.e., a temperature around the person (E)) as a valuable. Specifically, when temperature is put on the horizontal axis and value of the first parameter (i.e., value of LF/HF) is put on the vertical axis, a locus of values of the first parameter is defined as a parabola opening up.

In the graph (A) of FIG. 4, a first predetermined range including a minimum value xa is illustrated in a graph showing the characteristics of the first parameter. The first predetermined range is preset to be used for determining whether the person (E) feels comfortable or uncomfortable in the space (S). If the value of the first parameter is within the first predetermined range, this value is relatively low and the person (E) is relaxed. Hence, it can be determined that the person (E) feels comfortable in the space (S). If the value of the first parameter is out of the first predetermined range, this value is relatively high and the person (E) is excessively stressed. Hence, it can be determined that the person (E) feels uncomfortable in the space (S).

Note that the characteristics of the first parameter in the graph (A) of FIG. 4 vary between individuals. Hence, in one preferred embodiment, the memory for thermal sensation estimation (25) previously holds default data of the first parameter characteristic data set (26) indicating the characteristics of the first parameter. Preferably, the default data is corrected as appropriate depending on the person (E) using the space (S), and the corrected data is held separately as the first parameter characteristic data set (26) to be used for estimating the thermal sensation. The default data may be corrected as follows: Once or twice, for example, the person (E) is encouraged to enter the person (E)'s current thermal sensation via a touch panel (41) (described later). Based on the actually entered thermal sensation and a temperature in the space (S) when the thermal sensation is entered, a graph representing the default data is vertically and horizontally shifted in the graph (A) of FIG. 4.

—Second Parameter Characteristic Data Set—

The second parameter characteristic data set (27) indicates characteristics of a second parameter. The second parameter indicates any one of the following for the person (E): a coefficient of variation of R-R intervals (CVRR); a respiration rate (RR); or a heart rate (HR).

Here, the coefficient of variation of R-R intervals (CVRR) of the person (E) is a periodic variation in interval between R waves (i.e., heartbeat (pulse) interval) included in a heart rate signal. The respiration rate (RR) of the person (E) is a rate at which the person (E) breathes per unit time. The heart rate (HR) of the person (E) is a speed of heartbeat measured per unit time.

As seen in graphs (B) and (C) in FIG. 4, this second parameter is characterized to vary linearly, using a temperature in the space (S) (i.e., a temperature around the person (E)) as a variable. Specifically, any of the coefficient of variation of R-R intervals (CVRR), the respiration rate (RR), and the heart rate (HR) is in proportion temperature. Here, the graph (B) of FIG. 4 shows characteristics of the coefficient of variation of R-R intervals (CVRR), and the graph (C) of FIG. 4 shows characteristics of the respiration rate (RR) and the heart rate (HR).

The graph (B) in FIG. 4 shows that the coefficient of variation of R-R intervals (CVRR) is lower as the temperature is higher, and higher as the temperature is lower. The graph (C) in FIG. 4 shows that the respiration rate (RR) and the heart rate (HR) are higher as the temperature is higher, and lower as the temperature is lower. When the temperature in the space (S) is high and the person (E) feels relatively "hot", the amount of the person (E)'s perspiration tends to increase for thermoregulation and the rate of blood flow to peripheral skin tends to increase to encourage heat dissipation from the body. That is why the R-R intervals become short and the coefficient of variation of R-R intervals (CVRR) becomes small; whereas, the respiration rate (RR) and the heart rate (HR) become high. In contrast, when the temperature in the space (S) is low and the person (E) feels relatively "cold", the amount of the person (E)'s perspiration tends to decrease and the rate of blood flow to peripheral skin tends to decrease to reduce heat dissipation from the body. That is why the R-R intervals become long and the coefficient of variation of R-R intervals (CVRR) becomes large; whereas, the respiration rate (RR) and the heart rate (HR) become low.

In the graphs (B) and (C) of FIG. 4, a second predetermined range is illustrated in the graphs showing the characteristics of the second parameter. The second predetermined range is preset to be used for determining whether to proceed with operation for estimating the thermal sensation of the person (E).

With an attention focused on a temperature observed when the first parameter approximately has the minimum value xa, the second predetermined range in particular is preferably determined to have a predetermined width including values (points xb, xc) of the second parameter at the temperature. Then, if the first parameter is out of the first predetermined range, preferably, the second parameter is also determined to be out of the second predetermined range. If the values of the second parameter are close to the points xb and xc, the temperature in the space (S) is comfortable for the person (E) and the thermal sensation is close to "neither of them (neutral)". Hence, if the second parameter is within the second predetermined range, it can be determined that the operation for estimating the thermal sensation does not need to proceed. If the second parameter is out of the second predetermined range, the temperature in the space (S) is interpreted as uncomfortable for the person (E) and the thermal sensation is interpreted closer to "hot" or "cold" than to "neither of them (neutral)". Hence, it can be determined that the operation for estimating the thermal sensation needs to further proceed.

Note that the characteristics of the second parameter in the graphs (B) and (C) of FIG. 4 also vary between individuals. Hence, in one preferred embodiment, similar to the first parameter characteristic data set (26), the memory for thermal sensation estimation (25) previously holds default data of the second parameter characteristic data set (27) indicating the characteristics of the second parameter. Preferably, the default data is corrected as appropriate depending on the person (E) using the space (S), and the corrected data is held separately as the second parameter characteristic data set (27) to be used for estimating the thermal sensation. Note that as a technique to correct the default data, a technique similar to the previously described technique for correcting the first parameter characteristic data set (26) is used.

—CPU for Thermal Sensation Estimation—

The CPU for thermal sensation estimation (28) reads a program from the memory for thermal sensation estimation (25) and executes the program to function as a first parameter deriver (28a), a second parameter deriver (28b), and an estimator (28c) as illustrated in FIG. 2.

—First Parameter Deriver—The first parameter deriver (28a) derives the first parameter, based on the results of the measurements by the pressure-sensitive tube (21) and the microphone (23) included in the measurer.

When extracting the heart rate signal from the pressure signal output from the microphone (23), the first parameter deriver (28a) obtains the coefficient of variation of R-R intervals (CVRR) based on the heart rate signal. Specifically, while the person (E) sits on the seat (G11), the first parameter deriver (28a) calculates an R wave with large amplitude based on the heart rate signal. The first parameter deriver (28a) obtains a length of intervals between R waves; that is intervals between heartbeats (pulses), for each predetermined period, to calculate a periodic variation of the R-R intervals as the coefficient of variation of R-R intervals (CVRR).

Then, the first parameter deriver (28a) performs a frequency analysis on the calculated coefficient of variation of R-R intervals (CVRR) to obtain the low frequency component "LF" and the high frequency component "HF" in the coefficient of variation of R-R intervals (CVRR). The first parameter deriver (28a) then divides the low frequency component "LF" by the high frequency component "HF" to derive the first parameter (the ratio of the low frequency component to the high frequency component (LF/HF)).

—Second Parameter Derive—

The second parameter deriver (28b) derives the second parameter, based on the measurement results of the pressure-sensitive tube (21) and the microphone (23) included in the measurer.

If the second parameter to be derived is the coefficient of variation of R-R intervals (CVRR), the second parameter deriver (28b) obtains the coefficient of variation of R-R intervals (CVRR), using a similar technique used for the first parameter deriver (28a).

If the second parameter to be derived is the heart rate (RR), the second parameter deriver (28b) extracts a breathing signal from the pressure signal output from the microphone (23). From the extracted breathing signal, the second parameter deriver (28b) derives as the second parameter a rate at which the person (E) breathes per unit time (e.g., one minute).

If the second parameter to be derived is the heart rate (HR), the second parameter deriver (28b) extracts a heart rate signal from the pressure signal output from the microphone (23). From the extracted heart rate signal, the second parameter deriver (28b) derives as the second parameter a speed of heartbeat measured per unit time (e.g., one minute).

—Estimator—

The estimator (28c) estimates the thermal sensation of the person (E), using the first parameter derived by the first parameter deriver (28a) and the second parameter derived by the second parameter deriver (28b).

Specifically, the estimator (28c) applies the derived first parameter (the ratio of the low frequency component to the high frequency component (LF/HF)) to the first parameter characteristic data set (26) in the memory for thermal sensation estimation (25). As described above, the first parameter characteristic data set (26) is represented in the graph in the graph (A) of FIG. 4. The estimator (28c) applies the derived first parameter to the graph in the graph (A) of FIG. 4.

If the result of the application shows that the first parameter is within the first predetermined range, the estimator (28c) estimates that the person (E) feels (S) comfortable with the temperature of the space (S). In this case, the estimator (28c) can estimate that the thermal sensation of the person (E) is not "hot" or "cold" but "neither of them (neutral)." Note that the estimator (28c) may further apply the derived second parameter to the second parameter characteristic data set (27) to confirm that the second parameter is within the second predetermined range. When the second parameter is within the second predetermined range, the estimator (28c) can more reliably confirm that the thermal sensation of the person (E) is "neither of them (neutral)."

If the result of the application shows that the first parameter is out of the first predetermined range, the estimator (28c) estimates that the person (E) feels uncomfortable with the temperature of the space (S). In this case, the estimator (28c) can estimate that the thermal sensation of the person (E) is either "hot" or "cold." As clearly shown in the graph (A) of FIG. 4, however, the characteristics of the first parameter are defined as a parabola opening up. Hence, with the application of the first parameter to the first parameter characteristic data set (26) alone, it is difficult for the estimator (28c) to estimate which of "hot" or "cold" the thermal sensation of the person (E) is.

Thus, if the first parameter is out of the first predetermined range, the estimator (28c) determines whether the thermal sensation of the person (E) is either "hot" or "cold" based on the second parameter characteristic data set (27) in the memory for thermal sensation estimation (25) and the derived second parameter (i.e., any one of the coefficient of variation of R-R intervals (CVRR), the respiration rate (RR), or the heart rate (HR)). As described before, the second parameter characteristic data set (27) is represented in either the graph (B) or the graph (C) in FIG. 4. The estimator (28c) applies the derived second parameter to (i) the graph of (B) in FIG. 4 if the derived second parameter is the coefficient of variation of R-R intervals (CVRR), and (ii) the graph (C) in FIG. 4 if the derived second parameter is either the heart rate (HR) or the heart rate (HR).

If the result of the application shows that the second parameter is out of the second predetermined range, the estimator (28c) determines the thermal sensation of the person (E) from a position of the second parameter in either the graph (B) or the graph (C) in FIG. 4.

Specifically, when the second parameter is the coefficient of variation of R-R intervals (CVRR), if the coefficient of variation of R-R intervals (CVRR) is positioned on the right of the point xb and out of the second predetermined range (e.g., point xb1) in the graph (B) in FIG. 4, the estimator (28c) determines that the person (E) feels "hot" with the temperature of the space (S). If the coefficient of variation of R-R intervals (CVRR) is positioned on the left of the point xb and out of the second predetermined range (e.g., point xb2) in the graph (B) in FIG. 4, the estimator (28c) determines that the person (E) feels "cold" with the temperature of the space (S).

When the second parameter is either the respiration rate (RR) or the heart rate (HR), if the respiration rate (RR) or the heart rate (HR) is positioned on the right of the point xc and out of the second predetermined range (e.g., point xc1) in the graph (C) in FIG. 4, the estimator (28c) determines that the person (E) feels "hot" with the temperature of the space (S). If either the respiration rate (RR) or the heart rate (HR) is positioned on the left of the point xc and out of the second predetermined range (e.g., point xc2) in the graph (C) in FIG. 4, the estimator (28c) determines that the person (E) feels "cold" with the temperature of the space (S).

In summary, from the first parameter, the estimator (28c) determines whether the person (E) feels comfortable with the temperature in the space (S). If the person (E) feels uncomfortable with the temperature in the space (S), the estimator (28c) determines that the person (E) feels uncomfortable because the temperature is whether "hot" or "cold", using the second parameter. Thanks to such features, the air-conditioning control system (10) can correctly determine the thermal sensation of the person (E) with simple processing, from the body movement of the person (E) measured without restraining the person (E).

Note that if the second parameter is within the second predetermined range even though the first parameter is out of the first predetermined range, the estimator (28c) suspends the operation to determine whether the person (E) feels "hot" or "cold." In the case where the second parameter is within the second predetermined range even though the first parameter is out of the first predetermined range, some kind of problem is assumed to happen to either the derived first parameter or second parameter. If the above determination operation is carried out, using such a problematic parameter, the thermal sensation of the person (E) could be falsely determined. The operation of the air conditioner (A) would be controlled based on the result of the false determination, and the temperature in the space (S) would become undesirable for the person (E). Whereas, in this embodiment, the above determination operation is suspended if the second parameter is within the second predetermined range even though the first parameter is out of the first predetermined range. Hence, the temperature in the space (S) does not become undesirable for the person (E); instead, the temperature in the space (S) is maintained at a current temperature.

Preferably, the above thermal sensation estimation unit (20) continues the operation for estimating the thermal sensation of the person (E) for each predetermined time interval immediately after the person (E) entering the space (S) sits on the chair (G) until the person (E) gets out of the space (S).

Thermal sensation information indicating the thermal sensation of the person (E) estimated by thermal sensation estimation unit (20) is sent to the air-conditioning control unit (40).

—Air-Conditioning Controller—

The air-conditioning control unit (40) controls the operation of the air conditioner (A), based on the thermal sensation information sent from thermal sensation estimation unit (20). As illustrated in FIG. 2, the air-conditioning control unit (40) includes: the touch panel (41); a memory for air-conditioning control (43); and a CPU for air-conditioning control (48) (corresponding to an air-conditioning controller).

As illustrated in FIG. 1, the touch panel (41) is provided to, for example, a wall surface of the space (S). As illustrated in FIG. 2, the memory for air-conditioning control (43) and the CPU for air-conditioning control (48) are mounted on a printed board (P12). As illustrated in FIG. 1, the printed board (P12) is provided in a control box near the air conditioner (A).

Note that the printed board (P12) may be provided in the space (S).

—Touch Panel—The touch panel (41) is removably secured to a wall surface of the space (S). Through the touch panel (41), the person (E) can enter an instruction for operation of the air conditioner (A). The touch panel (41) displays various screens for the air conditioner (A).

Moreover, once or twice, the touch panel (41) may display a screen to encourage the person (E) to enter the current thermal sensation. The person (E) enters "hot", "cold", or "neither of them (neutral)" through the screen, so that the touch panel (41) can receive an actual thermal sensation of the person (E). The actually received thermal sensation is transmitted to the CPU for thermal sensation estimation (28) through the CPU for air-conditioning control (48). Based on the actual thermal sensation and temperature in the space (S), the CPU for thermal sensation estimation (28) can correct respective default data sets for the first parameter characteristic data set (26) and the second parameter characteristic data set (27). The correction makes the first and second parameter characteristic data sets (26, 27) more suitable to the person (E) currently in the room, improving precision in estimating the thermal sensation.

—Memory for Air-Conditioning Control—

The memory for air-conditioning control (43) includes such a semiconductor memory as a flash memory, and such a recording medium as a hard disc. The memory for air-conditioning control (43) stores a program to be read by the CPU for air-conditioning control (48) so that the CPU for air-conditioning control (48) executes the functions described below.

Moreover, the memory for air-conditioning control (43) may temporarily store such data as the first and second parameter characteristic data sets (26, 27) corrected by the CPU for thermal sensation estimation (28).

—CPU for Air-Conditioning Control—

The CPU for air-conditioning control (48) reads a program from the memory for air-conditioning control (43) and executes the read program to mainly function as the air-conditioning controller.

The CPU for air-conditioning control (48) controls an air-conditioning capacity of the air conditioner (A) based on thermal sensation information (i.e., the thermal sensation of the person (E) estimated by the estimator (28*c*) of thermal sensation estimation unit (20)). In particular, as the graph (A) in FIG. 4 shows, the CPU for air-conditioning control (48) determines, as a set temperature for the air conditioner (A), a temperature observed when the first parameter has the minimum value xa.

For example, if (i) the person (E) feels "uncomfortable" and "hot", and (ii) in FIG. 4, the first parameter shows the point xa1 and the second parameter shows either the point xb1 or the point xc1, the CPU for air-conditioning control (48) determines as the set temperature a temperature observed when the first parameter has the minimum value xa, and operates the air conditioner (A). Thus, the temperature in the space (S) falls by a temperature width Tw1 from the temperature observed when the first parameter has the point xa1 and the second parameter has either the point xb1 or the point xc1, and comes close to a temperature observed when the first parameter has the minimum value xa.

Moreover, if (i) the person (E) feels "uncomfortable" and "cold", and (ii) in FIG. 4, the first parameter shows the point xa2 and the second parameter shows either the point xb2 or the point xc2, the CPU for air-conditioning control (48) determines as the set temperature a temperature observed when the first parameter has the minimum value xa, and operates the air conditioner (A). Thus, the temperature in the space (S) rises by a temperature width Tw2 from the temperature observed when the first parameter shows the point xa2 and the second parameter shows either the point xb2 or the point xc2, and comes close to a temperature observed when the first parameter has the minimum value xa.

In the above control, the sense that the person (E) experiences for the temperature in the space (S) changes from "uncomfortable" to "comfortable", and the thermal sensation of the person (E) improves from "hot" or "cold" to "neither of them (neutral)."

Note that the above operation by the air-conditioning control unit (40) may be resumed based on the latest thermal sensation information for every predetermined time period (e.g., 10 minutes) elapsed since the determination of the set temperature.

<Operation of Air-Conditioning Control System>

Figure 5:
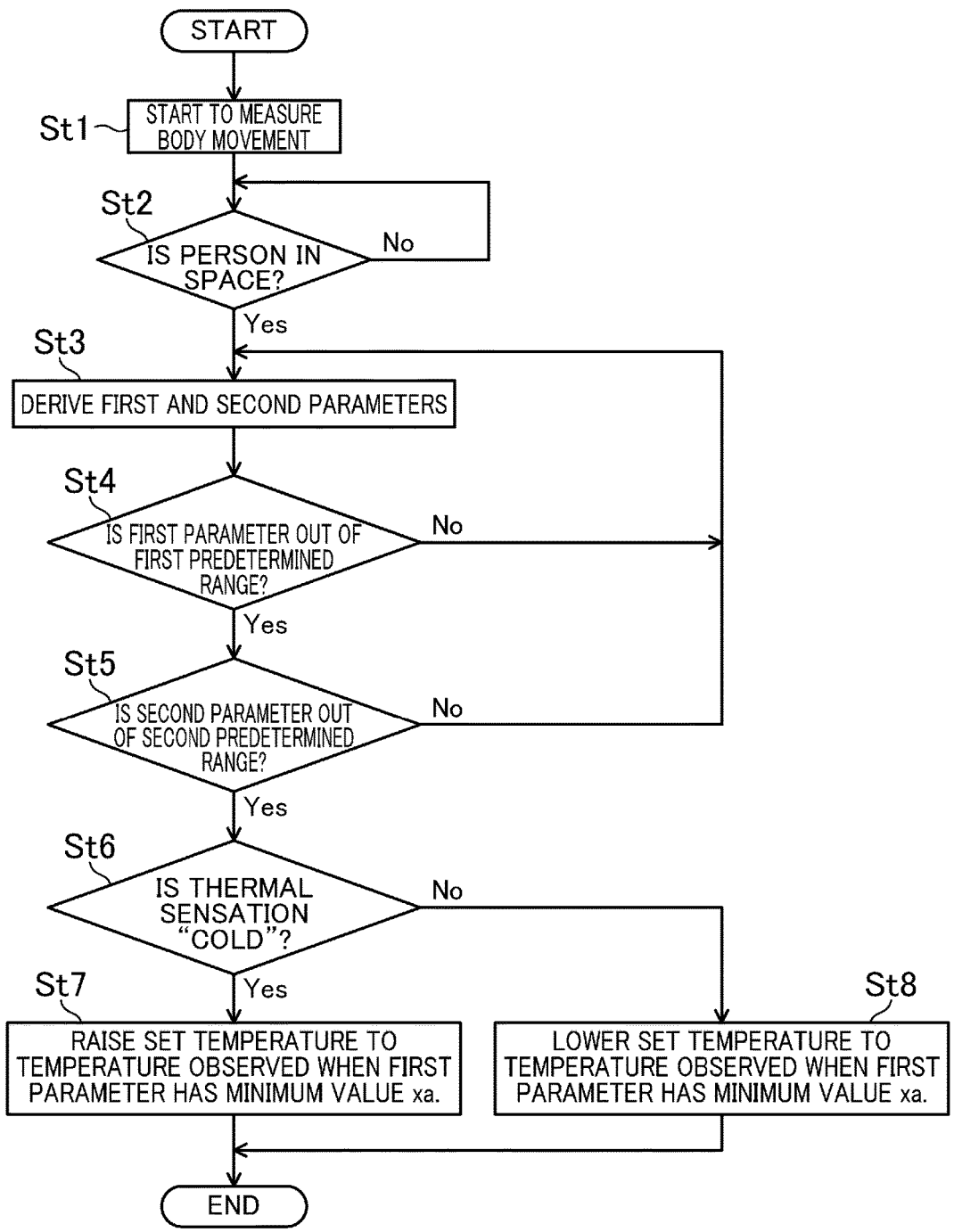
FIG. 5 is a flowchart showing a sequence of operation performed by the air-conditioning control system according to the first embodiment.

Briefly described below is a sequence of operation performed by the air-conditioning control system (10) according to this embodiment, with reference to FIG. 5.

Hereinafter, note that the first and second parameter characteristic data sets (26, 27) in the memory for thermal sensation estimation (25) already correspond to the person (E).

When the person (E) sits on the chair (G), the pressure-sensitive tube (21) receives pressure and the microphone (23) outputs a pressure signal depending on the pressure. Hence, a body movement of the person (E) starts to be measured (Step St1). Through the pressure signal output from the microphone (23), the CPU for thermal sensation estimation (28) determines that the person (E) is in the space (S) (Yes at Step St2).

Based on the pressure signal (i.e., a result of the measurement by the measurer) from the microphone (23), the first parameter deriver (28*a*) derives, as the first parameter, a ratio (LF/HF) of a low frequency component to a high frequency component in a coefficient of variation of R-R intervals (CVRR). Based on the pressure signal, the second parameter deriver (28*b*) derives, as the second parameter, any one of the coefficient of variation of R-R intervals (CVRR), the respiration rate (RR), or the heart rate (HR) of the person (E) (Step St3).

The estimator (28*c*) applies the derived first parameter to the first parameter characteristic data set (26) in the graph (A) of FIG. 4, and determines whether the first parameter is out of the first predetermined range (Step St4). If the first parameter is out of the first predetermined range (Yes at Step St4), the estimator (28*c*) applies the derived second parameter to the second parameter characteristic data set (27) in the graph (B) or the graph (C) in FIG. 4 to determine whether the second parameter is out of the second predetermined range (Step St5).

If the second parameter is out of the second predetermined range (Yes at Step St5), the estimator (28*c*) determines whether the person (E) feels "hot" or "cold" from a value of the second parameter (Step St6).

If the person (E) feels "cold" (Yes at Step St6), the CPU for air-conditioning control (48) raises a set temperature to a temperature observed when the first parameter has the minimum value xa, based on the first parameter characteristic data set (26) or the second parameter characteristic data set (27) (i.e., a graph in FIG. 4). If the person (E) feels "hot" (No at Step St6), the CPU for air-conditioning control (48) lowers the set temperature to the temperature observed when the first parameter has the minimum value xa, based on the first parameter characteristic data set (26) or the second parameter characteristic data set (27) (i.e., a graph in FIG. 4).

Thanks to this operation sequence, the air conditioner (A) operates in accordance with the set temperature determined in Steps St7 and St8 so that the temperature in the space (S) eventually comes to a level in which the person (E) feels comfortable.

Moreover, the air-conditioning control system (10) may at least measure a body movement and derive the first parameter after the predetermined time period has elapsed, to confirm that the first parameter is within the first predetermined range. This is to determine whether the comfort that the person (E) feels has improved.

Note that, if the first parameter is within the first predetermined range in Step St4 (No at Step St4), and the second parameter is within the second predetermined range in Step St5 (No at Step St5), the operation after Step St3 is repeated.

<Effects>

In this embodiment, the body movement of the person (E) is measured only by the measurer including the pressure-sensitive tube (21) and the microphone (23). From one of the results of the measurement, derived are (i) the first parameter (specifically, the ratio of the low frequency component to the high frequency component (LH/HF) in the coefficient of the variation of R-R intervals) of the person (E) and (ii) the second parameter (specifically, one of the coefficient of variation of R-R intervals (CVRR), the respiration rate (RR), or the heart rate (HR)) of the person (E). Then, the thermal sensation of the person (E) is estimated from the first parameter and the second parameter. Based on the estimated thermal sensation, the air conditioner (A) is controlled. Specifically, even though one measurer the minimum number of measures—is provided as a sensor, the air-conditioning control system (10) can obtain multiple parameters; namely the first and second parameters, for the person (E). Furthermore, the combination of the first and second parameters is a combination of (i) the ratio of the low frequency component to the high frequency component (LF/HF) which makes it possible to understand whether the person (E) feels uncomfortable and (ii) one of the indexes which relate to a condition of the body and the thermal sensation of the person (E); namely one of the coefficient of variation of R-R intervals (CVRR), the respiration rate (RR), or the heart rate (HR). Hence, using the combination of the parameters, the air-conditioning control system (10) can correctly obtain the thermal sensation of the person (E) to provide the space (S) with comfortable environment.

Moreover, in this embodiment, the measurer including the pressure-sensitive tube (21) and the microphone (23) measures body movement of the person (E) without restraining the person (E). Specifically, the measurer as a sensor is not always attached to the body of the person (E). Hence, the person (E) is free from an uncomfortable feeling caused when a sensor is always attached to the person (E). Such a feature reduces the risk that the sympathetic nerve is basically active so that the value of the first parameter is always high, making it possible to correctly determine whether a temperature in the space (S) is comfortable or uncomfortable.

Furthermore, the ratio of the low frequency component to the high frequency component (LF/HF); namely the first parameter, is an index representing whether the person (E) feels comfortable or uncomfortable. As the graph (A) in FIG. 4 shows, the first parameter is characterized to be represented in a quadratic function opening up where the temperature is a variable. If the first parameter is out of the first predetermined range, the estimator (28c) can determine that the person (E) feels uncomfortable. Meanwhile, as the illustrations (B) and (C) show, the second parameter; namely any one of the coefficient of variation of R-R intervals (CVRR), the respiration rate (RR), or the heart rate (HR), is characterized to vary linearly where the temperature is a variable. Hence, from a value of the second parameter, the estimator (28c) can determine the reason why the person (E) feels uncomfortable is whether the space (S) is "hot" or "cold". Using the first parameter characterized to be represented in a quadratic function where the temperature is a variable and the second parameter characterized to be represented in a straight line where the temperature is the variable, the air-conditioning control system (10) can correctly determine the thermal sensation of the person (E).

Particularly, in this embodiment, if the first parameter is out of the first predetermined range and the second parameter is also out of the second predetermined range, the measured body movement and the derived first and second parameters can be determined as normal values. Use of the normal first and second parameters makes it possible to estimate the thermal sensation of the person (E) and control the operation of air conditioner (A) with accuracy.

In the case where the second parameter is within the second predetermined range even though the first parameter is out of the first predetermined range, some kind of problem is assumed to happen to either the derived first parameter or second parameter. If the above determination operation is carried out using such a problematic parameter, the estimator (28c) could falsely determine whether the person (E) feels hot or cold. Based on the result of the false determination, the air-conditioning control system (10) would cause the air conditioner (A) to carry out undesirable operation for the person (E). Whereas, in this embodiment, the determination operation is suspended if the second parameter is within the second predetermined range even though the first parameter is out of the first predetermined range. Such a feature can avoid the use of a problematic parameter followed by false determination of the thermal sensation of the person (E), and operation of the air conditioner (A) based on the result of the false determination.

Furthermore, the CPU for air-conditioning control (48) determines, as a set temperature for the air conditioner (A), a temperature observed when the first parameter has the minimum value xa. The temperature observed when the first parameter has the minimum value xa is to be a temperature for the person (E) to feel comfortable. Hence, the temperature in the space (S) eventually comes to a level in which the person (E) feels comfortable.

Second Embodiment

Described next is a case in which multiple people (E) are in the space (S).

Figure 6:
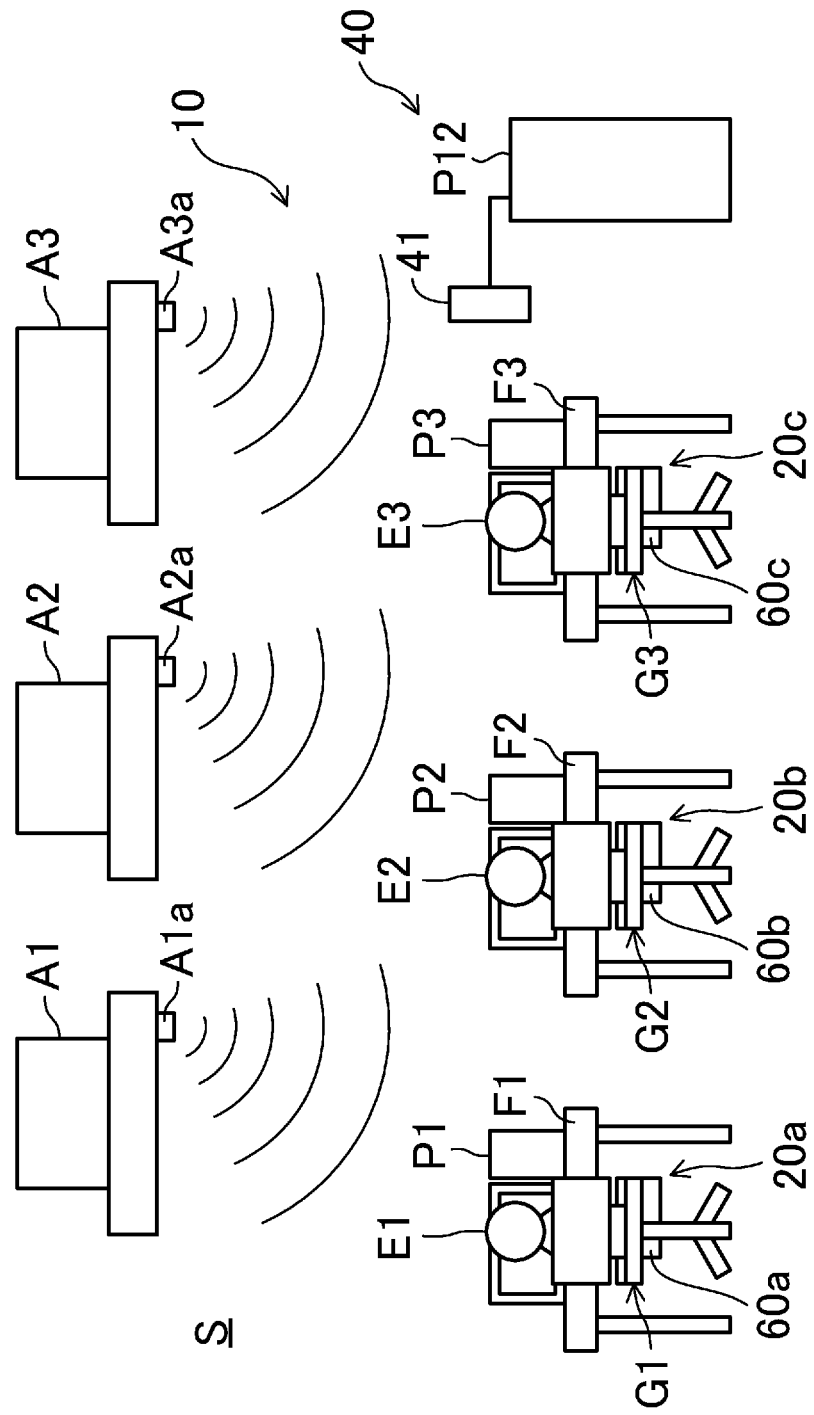
FIG. 6 is a schematic view illustrating a configuration of an air-conditioning control system according to a second embodiment.

The space (S) in this embodiment is larger than that in the first embodiment. In the space (S), three air conditioners (A1, A2, A3) are mounted in the ceiling as illustrated in FIG. 6. Furthermore, in the space (5), three desks (F1, F2, F3) and three chairs (G1, G2, G3) are provided for three respective people (E1, E2, E3) in a room. Personal Computers (P1, P2, P3) are placed on the respective desks (F1, F2, F3).

<Configuration of Air-Conditioning Control System>

As illustrated in FIG. 6, the air-conditioning control system (10) includes: three thermal sensation estimation units (20a, 20b, 20c) and one air-conditioning control unit (40).

The thermal sensation estimation units (20a, 20b, 20c) are provided for the respective chairs (G1, G2, G3). The thermal sensation estimation units (20a, 20b, 20c) are the same in configuration with one another and as the thermal sensation estimation unit (20) according to the above first embodiment.

Figure 7:
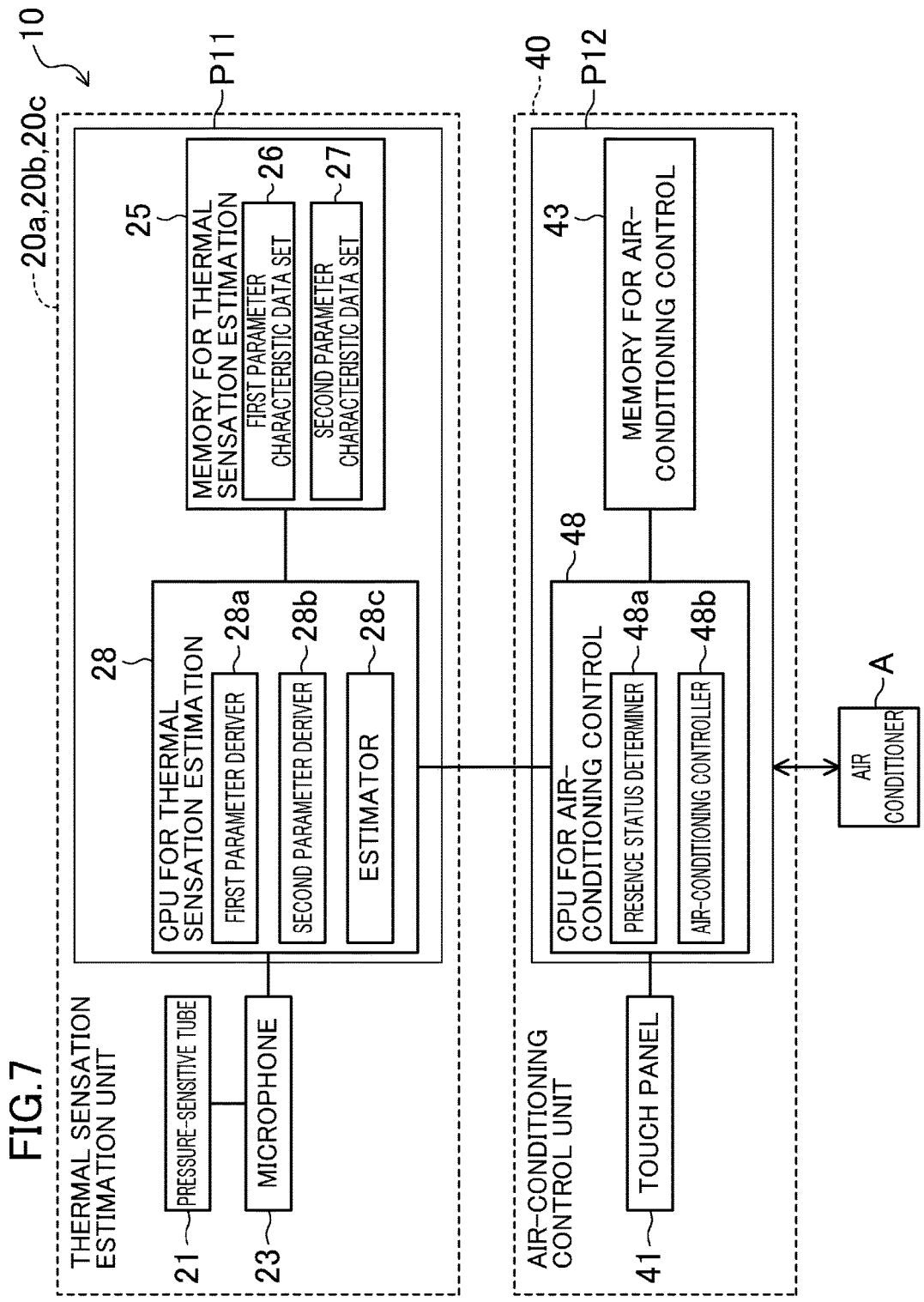
FIG. 7 is a block diagram schematically illustrating a configuration of the air-conditioning control system according to the second embodiment.

As illustrated in FIG. 7, each of the thermal sensation estimation units (20a, 20b, 20c) includes: the pressure-sensitive tube (21); the microphone (23); the memory for thermal sensation estimation (25); and the CPU for thermal sensation estimation (28). The pressure-sensitive tube (21) and the microphone (23) correspond to a measurer. The pressure-sensitive tube (21) and the microphone (23) measure a body movement of the people (E1, E2, E3) sitting on the corresponding chairs (G1, G2, G3). The memory for thermal sensation estimation (25) stores the first parameter characteristic data set (26) according to the graph (A) in FIG. 4, and the second parameter characteristic data set (27) according to the graphs (B) and (C) in FIG. 4. The memory for thermal sensation estimation (25) and the CPU for thermal sensation estimation (28) are mounted on the single printed board (P11). The CPU for thermal sensation estimation (28) functions as the first parameter deriver (28a), the second parameter deriver (28b), and the estimator (28c).

The air-conditioning control unit (40) includes: the touch panel (41) provided in the space (S); the memory for air-conditioning control (43); and the CPU for air-conditioning control (48). The memory for air-conditioning control (43) and the CPU for air-conditioning control (48) are mounted on the single printed board (P12). In particular, the CPU for air-conditioning control (48) functions as a presence status determiner (48a) and an air-conditioning controller (48b).

Based on a body movement of each of the people (E1, E2, E3) measured by the pressure-sensitive tube (21) and the microphone (23), the presence status determiner (48a) determines a presence status of the people (E1, E2, E3) sitting on the chairs (G1, G2, G3). Measuring a body movement of each of the people (E1, E2, E3) by the measurer; namely the pressure-sensitive tube (21) and the microphone (23), is interpreted that the people (E1, E2, E3) are sitting on the chairs (G1, G2, G3) each provided with the pressure-sensitive tube (21) and the microphone (23). Hence, the presence status determiner (48a) can determine whether the chairs (G1, G2, G3) are occupied.

Similar to the CPU for air-conditioning control (48) according to the above first embodiment, the air-conditioning controller (48b) controls air-conditioning capacities of the air conditioners (A1,A2,A3) based on an estimated thermal sensation for each of the people (E1, E2, E3). More specifically, the air-conditioning controller (48b) determines a set temperature for each of the air conditioners (A1, A2, A3) to be a temperature observed when a first parameter has the minimum value xa.

Note that, in this embodiment, the thermal sensation estimation units (20a, 20b, 20c) and the air-conditioning control unit (40) are communicably connected to each other not via wires but via radio waves.

<How to Detect Seating Position>

In this embodiment, seating information on the chairs (G1, G2, G3) and people (E1, E2, E3) is not previously obtained. Instead, the position information is detected and obtained at different times. Hence, described below is how to detect a seating position according to this embodiment.

As illustrated in FIG. 6, each air conditioner (A1, A2, A3) is provided with one wireless appliance for air conditioner (A1a, A2a, A3a) functioning as an access point or employing Bluetooth (trade name) Low Energy (BLE). Other than the thermal sensation estimation units (20a, 20b, 20c), each chair (G1, G2, G3) is provided with one wireless appliance for chair (60a, 60b, 60c). The wireless appliances for chair (60a, 60b, 60c) are connected to the respective thermal sensation estimation units (20a, 20b, 20c). The wireless appliances for chair (60a, 60b, 60c) employ such a standard as Wi-Fi.

The wireless appliances for air conditioner (A1a, A2a, A3a) constantly broadcast such information as identification information and position information on the corresponding air conditioners (A1, A2, A3). Hence, the air conditioners (A1, A2, A3) are spaced apart from one another at a predetermined distance, so that the wireless appliances for air conditioner (A1a, A2a, A3a) do not cause radio interference with one another.

When receiving information which the wireless appliances for air conditioner (A1a, A2a, A3a) are broadcasting, the wireless appliances for chair (60a, 60b, 60c) transmit, to the air-conditioning control unit (40), a signal indicating the reception of the information, and, if any, a pressure signal indicating body movements of the people (E1, E2, E3) measured by the thermal sensation estimation units (20a, 20b, 20c).

Such a feature allows the air-conditioning control unit (40) to receive signals indicating the measured body movements of the people (E1, E2, E3) and signals indicating that the wireless appliances for chair (60a, 60b, 60c) have received information from the wireless appliances for air conditioner (A1a, A2a, A3a). The presence status determiner (48a) of the air-conditioning control unit (40) can aggregate these signals to obtain positional relationships between the air conditioners (A1, A2, A3) and the respective chairs (G1, G2, G3), and, based on the fact that the body movements have already been measured, to determine a presence status; namely, current seating information on the people (E1, E2, E3) sitting on the chairs (G1, G2, G3).

<Operation of Air-Conditioning Control System>

Described below is a sequence of operation performed by the air-conditioning control system (10) according to this embodiment, with reference to FIG. 8.

Hereinafter, note that the first and second parameter characteristic data sets (26, 27) in the memory for thermal sensation estimation (25) already correspond to the people (E1, E2, E3).

When the people (E1, E2, E3) sit on the chairs (G1, G2, G3), the pressure-sensitive tubes (21) receive pressure and the microphones (23) output a pressure signal depending on the pressure. The thermal sensation estimation units (20a, 20b, 20c) start to measure a body movement of the sitting people (E1, E2, E3) (Step St11).

When receiving information broadcasted from the wireless appliances for air conditioner (A1a, A2a, A3a), the wireless appliances for chair (60a, 60b, 60c) transmit a signal indicating the reception of the information, and a signal on the body movement (the pressure signal) representing a result of the measurement to the air-conditioning control unit (40). Based on these signals, the presence status determiner (48a) of the air-conditioning control unit (40) obtains positional relationships between the air conditioners (A1, A2, A3) and the respective chairs (G1, G2, G3), and determines a presence status of the people (E1, E2, E3) sitting on the chairs (G1, G2, G3) (Step St12). Specifically, the presence determiner (48a) determines that the people (E1, E2, E3) are sitting on the chairs (G1, G2, G3) at which the body movement has been measured. A thermal sensation of people (E1, E2, E3) who are determined to be sitting is determined as a factor to be included for the control of the air-conditioning capacities.

Meanwhile, based on the pressure signal from the microphone (23) (i.e., the signal on the body movement of the sitting people (E1, E2, E3)), the first parameter deriver (28a)

of each of the thermal sensation estimation units (20a, 20b, 20c) derives, as the first parameter, a ratio of the low frequency component to high frequency component (LF/HF) in a variation of R-R intervals. In a similar manner, based on the pressure signal from the microphone (23), the second parameter deriver (28b) derives, as the second parameter, any one of a coefficient of variation of R-R intervals (CVRR), a respiration rate (RR), or a heart rate (HR) of the people (E1, E2, E3) (Step St13).

The estimator (28c) applies the derived first parameter to the first parameter characteristic data set (26), corresponding to one of the people (E1, E2, E3), in the graph (A) of FIG. 4, and determines whether the first parameter is out of the first predetermined range (Step St4). If the first parameter is out of the first predetermined range (Yes at Step St14), the estimator (28c) applies the derived second parameter to the second parameter characteristic data set (27), corresponding to one of the people (E1, E2, E3), in the graph (B) or the graph (C) in FIG. 4 to determine whether the second parameter is out of the second predetermined range (Step St15).

If the second parameter is out of the second predetermined range (Yes at Step St15), the estimator (28c) determines whether the corresponding person (one of E1, E2, E3) feels "hot" or "cold" from a value of the second parameter (Step St16). The thermal sensation estimation units (20a, 20b, 20c) sequentially transmit, to the air-conditioning control unit (40), results of comparisons between the predetermined ranges of the parameters and results of determinations of thermal sensations.

The thermal sensation estimation units (20a, 20b, 20c) repeat the operation Step St13 through Step St16 until operation for deriving the parameters and operation for estimating the thermal sensations end (No at Step St17) for all the people (E1, E2, E3) currently sitting on the chairs (G1, G2, G3).

By the time the thermal sensation estimation units (20a, 20b, 20c) finish the operation for deriving the parameters and the operation for estimating the thermal sensations for all the people (E1, E2, E3), the air-conditioning controller (48b) of the air-conditioning control unit (40) has already received the results of the comparisons between the predetermined ranges of the parameters and the results of the determinations of the thermal sensations for all the sitting people (E1, E2, E3) (Yes at Step St17). In this case, the air-conditioning controller (48b) determines whether the number of people (E1, E2, E3) whose first parameters are within the first predetermined range is equal to or smaller than a predetermined number, and which of the thermal sensations "cold" or "hot" more people (E1, E2, E3) feel (Steps St18 and St19).

More specifically, if more people (E1, E2, E3) feel "uncomfortable" than "comfortable" with the temperature of the space (S) (Yes at Step St18), the air-conditioning controller (48b) controls the air-conditioning capacity of the air conditioner (A) by determining which thermal sensation a majority of the more people (E1, E2, E3) feel (Step St19). In other words, if more people (E1, E2, E3) have a thermal sensation of either "hot" or "cold" than a thermal sensation of "neither of them (neutral)", the air-conditioning controller (48b) controls the air-conditioning capacity in accordance with the thermal sensation of either "hot" or "cold" shared with the majority of the people (E1, E2, E3) having the thermal sensation of either "hot" or "cold." Note that the predetermined number is previously determined as appropriate.

If the number of the people (E1, E2, E3) whose first parameters are within the first predetermined range (i.e., the number of people (E1, E2, E3) feeling comfortable) is equal to or smaller than the predetermined number (Yes at Step St18) and more people (E1, E2, E3) have the thermal sensation "cold" (Yes at Step St19), the air-conditioning controller (48b) raises the set temperature of the air conditioner (A) above the current set temperature (Step St20). For example, the air-conditioning controller (48b) can calculate temperatures to be observed when the first parameters have the minimum value xa, from the first parameter characteristic data sets (26) and the second parameter characteristic data sets (27) corresponding to the respective people (E1, E2, E3) feeling "cold". Then, the air-conditioning controller (48b) can raise the set temperature to the average of the calculated temperatures.

If the number of the people (E1, E2, E3) whose first parameters are within the first predetermined range (i.e., the number of people (E1, E2, E3) feeling comfortable) is equal to or smaller than the predetermined number (Yes at Step St18) and more people (E1, E2, E3) have the thermal sensation "hot" (No at Step St19), the air-conditioning controller (48b) lowers the set temperature of the air conditioner (A) below the current set temperature (Step St21). For example, the air-conditioning controller (48b) can calculate temperatures to be observed when the first parameters have the minimum value xa, from the first parameter characteristic data sets (26) and the second parameter characteristic data sets (27) corresponding to the respective people (E1, E2, E3) feeling "hot". Then, the air-conditioning controller (48b) can lower the set temperature to the average of the calculated temperatures.

Thanks to this operation sequence, the air conditioner (A) operates in accordance with the set temperature determined at Steps St20 and St21 so that the temperature in the space (S) eventually comes to a level in which a majority of the people (E1, E2, E3) feels comfortable.

Note that the air-conditioning control system (10) may at least measure a body movement and derive the first parameters after the predetermined time period has elapsed to confirm that the first parameters are within the first predetermined range. This is to determine whether the comfort that the people feel has improved.

Note that, if the first parameters are within the first predetermined range in Step St14 (No at Step St14), and the second parameters are within the second predetermined range in Step St15 (No at Step St15), the operation after Step St13 is repeated.

If the number of the people (E1, E2, E3) whose first parameters are within the first predetermined range is larger than a target number (No at Step St18), more people (E1, E2, E3) feel "comfortable" than "uncomfortable" with the current temperature in the space (S). Here, the air-conditioning control unit (40) does not change the set temperature to maintain the current temperature in the space (S).

<Effects>

This embodiment has effects below, in addition to those in the above first embodiment.

In this embodiment, if multiple people (E1, E2, E3) are in the space (S), the operation of the air conditioner (A) is controlled in accordance with a thermal sensation of either "hot" or "cold" shared with a majority of the people (E1, E2, E3) having the thermal sensation of either "hot" or "cold." Such a feature provides the space (S) with a comfortable environment for the majority of the people (E1, E2, E3).

Moreover, in this embodiment, the body movements of the people (E1, E2, E3) are easily measured while the people (E1, E2, E3) are simply sitting on the chairs (G1, G2, G3). Based on the measured movements, a presence status of the people (E1, E2, E3) can be determined. The thermal sensations of the people (E1, E2, E3) sitting on the chairs (G1, G2, G3) are the factors to be included for the control of the air-conditioning capacity. Such a feature eliminates the need for previously storing, in the memory for air-conditioning control (43), position information on the chairs (G1, G2, G3) and the people (E1, E2, E3). Moreover, even if the people (E1, E2, E3) temporarily sit on different chairs (G1, G2, G3), the air-conditioning control system (10) can obtain thermal sensations of the people (E1, E2, E3) sitting on the different chairs (G1, G2, G3) at that moment.

Other Embodiments

The above first and second embodiments may also be configured as follows.

When estimating a thermal sensation, the estimator (28c) does not necessarily have to determine whether the first parameter is out of the first predetermined range and the second parameter is out of the second predetermined range. If the first parameter is out of the first predetermined range and the second parameter is within the second predetermined range, the operation for estimating the thermal sensation does not necessarily have to be suspended.

When the determinations whether the first parameter is out of the first predetermined range and the second parameter is out of the second predetermined range are made, the order of the determinations shall not be limited to the ones in the first and second embodiments. The determination for the second parameter may precede the determination for the first parameter.

In the control of the air-conditioning capacity of the air conditioner (A), all that is required is that the person (E) feels the space (S) changing from "uncomfortable" to "comfortable." Hence, the set temperature may be determined to be another temperature than the temperature observed when the first parameter has the minimum value xa.

In the above second embodiment, if multiple people (E1, E2, E3) are found, the air-conditioning capacity of the air conditioner (A) is controlled in accordance with a thermal sensation (i.e., either "hot" or "cold") shared with a majority of the people (E1, E2, E3). However, the air-conditioning capacity is not necessarily controlled in this manner. For example, the space (S) may be divided into multiple air-conditioning zones in accordance with thermal sensations of the people (E1, E2, E3). Then, the air-conditioning capacity of the air conditioner (A) may be controlled for each of the air-conditioning zones.

In the second embodiment, how to detect a seating position is described with reference to FIG. 6. However, this technique is not necessarily adopted. Moreover, if the seating position detection technique per se is not carried out, preferably, the memory for air-conditioning control (43) previously stores the seating information on the chairs (G1, G2, G3) and the people (E1, E2, E3).

A body movement of the person (E) may be measured while at least a part of the person (E) is restrained.

INDUSTRIAL APPLICABILITY

As described above, the present invention is useful for a system to correctly obtain a thermal sensation of a person in a room to provide a comfortable environment.

DESCRIPTION OF REFERENCE CHARACTERS

10 Air-Conditioning Control System
21 Pressure-Sensitive Tube (Measurer)
23 Microphone (Measurer)
28a First Parameter Deriver
28b Second Parameter Deriver
28c Estimator
48 CPU for Air-Conditioning Control (Air-Conditioning Controller)
48a Presence Status Determiner
48b Air-Conditioning Controller

The invention claimed is:

1. An air-conditioning control system comprising:
a measurer measuring a body movement of a person in a room a space of which is to be air-conditioned by an air conditioner;
a first parameter deriver deriving, as a first parameter, a ratio of a low frequency component to a high frequency component in a variation of R-R intervals of the person, based on a result of the measurement by the measurer;
a second parameter deriver deriving, as a second parameter, any one of a coefficient of variation of R-R intervals, a respiration rate, or a heart rate of the person, based on the result of the measurement by the measurer;
an estimator estimating a thermal sensation of the person, based on the first parameter and the second parameter; and
an air-conditioning controller controlling an air-conditioning capacity of the air conditioner, based on a result of the estimation by the estimator, wherein
the first parameter is characterized to be represented in a quadratic function opening up where a temperature in the space is a variable,
the second parameter is characterized to vary linearly where the temperature in the space is the variable, and
if the first parameter is out of a first predetermined range, the estimator carries out operation to determine, based on the second parameter, whether the thermal sensation of the person is hot or cold.

2. The air-conditioning control system of claim 1, wherein the measurer measures the body movement of the person without restraining the person.

3. The air-conditioning control system of claim 1, wherein the estimator carries out the operation if the second parameter is out of a second predetermined range.

4. The air-conditioning control system of claim 3, wherein the estimator suspends the operation if the second parameter is within the second predetermined range.

5. The air-conditioning control system of claim 1, wherein the air-conditioning controller determines, as a set temperature for the air conditioner, a temperature observed when the first parameter represented in the quadratic function has a minimum value.

6. The air-conditioning control system of claim 1, wherein
if the person includes people, and the people are in the space,
for each of the people, the first parameter deriver derives the first parameter and the second parameter deriver derives the second parameter,
the estimator estimates a thermal sensation for each of the people, using the first parameter and the second parameter for each of the people, and
if more than a predetermined number of the people have the thermal sensation of either hot or cold, the air-conditioning controller controls the air-conditioning capacity of the air conditioner in accordance with the thermal sensation of either hot or cold shared with a majority of the people having the thermal sensation of either hot or cold.

7. The air-conditioning control system of claim 6, wherein the measurer includes measurers, and each of the measurers is provided to a corresponding one of chairs in the space, and measures a body movement of the people sitting on the chairs, the air-conditioning control system further comprising a presence status determiner determining a presence status of the people sitting on the chairs, based on a result of the measurements by the measurers.

* * * * *